US008630932B1

United States Patent
Lapsley et al.

(10) Patent No.: US 8,630,932 B1
(45) Date of Patent: *Jan. 14, 2014

(54) BIOMETRIC FINANCIAL TRANSACTION SYSTEM AND METHOD

(75) Inventors: Philip D. Lapsley, Oakland, CA (US); Philip J. Gioia, Corte Madera, CA (US); Michael Kleeman, Corte Madera, CA (US)

(73) Assignee: Open Invention Network, LLC, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/587,708

(22) Filed: Aug. 16, 2012

Related U.S. Application Data

(60) Continuation of application No. 13/284,219, filed on Oct. 28, 2011, now Pat. No. 8,452,680, which is a continuation of application No. 13/108,703, filed on May 16, 2011, now Pat. No. 8,073,756, which is a continuation of application No. 12/423,628, filed on Apr. 14, 2009, now Pat. No. 7,970,678, which is a division of application No. 09/871,241, filed on May 30, 2001, now Pat. No. 7,565,329.

(60) Provisional application No. 60/208,680, filed on May 31, 2000.

(51) Int. Cl.
*G06Q 40/00* (2012.01)

(52) U.S. Cl.
USPC ........ 705/35; 705/3; 705/44; 705/67; 705/75; 705/76; 715/811; 713/186; 702/104; 382/100; 382/115; 382/126; 380/258; 379/145; 340/426.19; 235/492; 435/5

(58) Field of Classification Search
USPC ............. 705/3, 44, 67, 75, 76; 715/811; 713/186; 702/104; 382/100, 115, 126; 380/258; 379/145; 340/426.19; 235/492; 435/5
See application file for complete search history.

(56) References Cited

U.S. PATENT DOCUMENTS

| 3,639,905 A | 2/1972 | Yaida et al. |
| 3,876,864 A | 4/1975 | Clark et al. |

(Continued)

FOREIGN PATENT DOCUMENTS

| EP | 0581421 A1 | 2/1994 |
| EP | 0598469 A2 | 5/1994 |

(Continued)

OTHER PUBLICATIONS

Anderson, Teresa, et al., "Security Works," Security Management, v. 27, No. 11, Nov. 1993, pp. 17-19.

(Continued)

*Primary Examiner* — James Trammell
*Assistant Examiner* — Sanjeev Malhotra
(74) *Attorney, Agent, or Firm* — Haynes and Boone, LLP

(57) ABSTRACT

Tokenless biometric authorization of transaction between a consumer and a merchant uses an identicator and an access device. A consumer registers with the identicator a biometric sample taken from the consumer. The consumer and merchant establish communications via the access device. The merchant proposes a transaction to the consumer via the access device. The access device communicates to the merchant associated with the access device. After the consumer and merchant have agreed on the transaction, the consumer and the identicator use the access device to establish communications. The access device communicates to the identicator the code associated with the access device. The identicator compares biometric sample from the consumer with registered biometric sample. Upon successful identification, the identicator forwards information regarding the consumer to the merchant. These steps accomplish a biometrically authorized electronic financial transaction without the consumer having to present any personalized man-made memory tokens.

17 Claims, 2 Drawing Sheets

(56) References Cited

U.S. PATENT DOCUMENTS

| | | |
|---|---|---|
| 3,943,335 A | 3/1976 | Kinker et al. |
| 3,975,711 A | 8/1976 | McMahon |
| 4,048,618 A | 9/1977 | Hendry |
| 4,151,512 A | 4/1979 | Riganati et al. |
| 4,208,651 A | 6/1980 | McMahon |
| 4,213,038 A | 7/1980 | Silverman et al. |
| 4,227,805 A | 10/1980 | Schiller |
| 4,253,086 A | 2/1981 | Szwarcbier |
| 4,321,672 A | 3/1982 | Braun et al. |
| 4,322,163 A | 3/1982 | Schiller |
| 4,353,056 A | 10/1982 | Tsikos |
| 4,358,677 A | 11/1982 | Ruell et al. |
| 4,390,968 A | 6/1983 | Hennessy et al. |
| 4,429,413 A | 1/1984 | Edwards |
| 4,484,328 A | 11/1984 | Schlafly |
| 4,537,484 A | 8/1985 | Fowler et al. |
| 4,544,267 A | 10/1985 | Schiller |
| 4,582,985 A | 4/1986 | Lofberg |
| 4,618,988 A | 10/1986 | Schiller |
| 4,649,563 A | 3/1987 | Riskin |
| 4,675,815 A | 6/1987 | Kuroki et al. |
| 4,696,046 A | 9/1987 | Schiller |
| 4,699,149 A | 10/1987 | Rice |
| 4,720,869 A | 1/1988 | Wadia |
| 4,728,186 A | 3/1988 | Eguchi et al. |
| 4,734,858 A | 3/1988 | Schlafly |
| 4,747,050 A | 5/1988 | Brachtl et al. |
| 4,752,966 A | 6/1988 | Schiller |
| D298,536 S | 11/1988 | Brefka |
| 4,784,484 A | 11/1988 | Jensen |
| 4,790,564 A | 12/1988 | Larcher et al. |
| 4,799,156 A | 1/1989 | Shavit et al. |
| 4,805,223 A | 2/1989 | Denyer |
| 4,821,118 A | 4/1989 | Lafreniere |
| 4,837,422 A | 6/1989 | Dethloff et al. |
| 4,845,636 A | 7/1989 | Walker |
| 4,868,376 A | 9/1989 | Lessin et al. |
| 4,926,480 A | 5/1990 | Chaum |
| 4,946,276 A | 8/1990 | Chilcott |
| 4,947,028 A | 8/1990 | Gorog |
| 4,947,443 A | 8/1990 | Costello |
| 4,961,142 A | 10/1990 | Elliott et al. |
| 4,993,068 A | 2/1991 | Piosenka et al. |
| 4,995,086 A | 2/1991 | Lilley et al. |
| 4,998,279 A | 3/1991 | Weiss |
| 5,025,372 A | 6/1991 | Burton |
| 5,036,461 A | 7/1991 | Elliott et al. |
| 5,054,089 A | 10/1991 | Uchida et al. |
| 5,054,090 A | 10/1991 | Knight et al. |
| 5,056,019 A | 10/1991 | Schultz et al. |
| 5,073,950 A | 12/1991 | Colbert et al. |
| 5,077,803 A | 12/1991 | Kato et al. |
| 5,088,817 A | 2/1992 | Igaki et al. |
| 5,095,194 A | 3/1992 | Barbanell |
| 5,103,486 A | 4/1992 | Grippi |
| 5,105,467 A | 4/1992 | Kim et al. |
| 5,109,427 A | 4/1992 | Yang |
| 5,109,428 A | 4/1992 | Igaki et al. |
| 5,144,680 A | 9/1992 | Kobayashi et al. |
| 5,146,102 A | 9/1992 | Higuchi et al. |
| 5,161,204 A | 11/1992 | Hutcheson et al. |
| 5,168,520 A | 12/1992 | Weiss |
| 5,180,901 A | 1/1993 | Hiramatsu |
| 5,191,611 A | 3/1993 | Lang |
| 5,210,588 A | 5/1993 | Lee |
| 5,210,797 A | 5/1993 | Usui et al. |
| 5,222,152 A | 6/1993 | Fishbine et al. |
| 5,224,164 A | 6/1993 | Eisner |
| 5,224,173 A | 6/1993 | Kuhns et al. |
| 5,229,764 A | 7/1993 | Matchett et al. |
| 5,230,025 A | 7/1993 | Fishbine et al. |
| 5,239,583 A | 8/1993 | Parrillo |
| 5,241,606 A | 8/1993 | Horie |
| 5,251,259 A | 10/1993 | Mosley |
| D340,919 S | 11/1993 | Lee |
| 5,265,162 A | 11/1993 | Bush et al. |
| 5,267,324 A | 11/1993 | Kumagai |
| 5,274,695 A | 12/1993 | Green |
| 5,276,314 A | 1/1994 | Martino et al. |
| 5,280,527 A | 1/1994 | Gullman et al. |
| 5,280,627 A | 1/1994 | Flaherty et al. |
| 5,321,242 A | 6/1994 | Heath, Jr. |
| 5,321,765 A | 6/1994 | Costello |
| 5,325,442 A | 6/1994 | Knapp |
| 5,329,589 A | 7/1994 | Fraser et al. |
| 5,335,288 A | 8/1994 | Faulkner |
| 5,343,529 A | 8/1994 | Goldfine et al. |
| 5,351,303 A | 9/1994 | Willmore |
| 5,354,974 A | 10/1994 | Eisenberg |
| 5,359,669 A | 10/1994 | Shanley |
| 5,371,794 A | 12/1994 | Diffie et al. |
| 5,371,797 A | 12/1994 | Bocinsly, Jr. |
| 5,383,113 A | 1/1995 | Kight et al. |
| 5,386,104 A | 1/1995 | Sime |
| 5,400,662 A | 3/1995 | Tamori |
| 5,412,738 A | 5/1995 | Brunelli et al. |
| 5,416,573 A | 5/1995 | Sartor, Jr. |
| 5,429,006 A | 7/1995 | Tamori |
| 5,457,747 A | 10/1995 | Drexler |
| 5,465,290 A | 11/1995 | Hampton et al. |
| 5,465,303 A | 11/1995 | Levison et al. |
| 5,466,919 A | 11/1995 | Havakimian |
| 5,469,506 A | 11/1995 | Berson et al. |
| 5,484,988 A | 1/1996 | Hills et al. |
| 5,485,510 A * | 1/1996 | Colbert .................. 379/145 |
| D367,044 S | 2/1996 | Arakaki |
| 5,493,621 A | 2/1996 | Matsumura |
| 5,499,288 A | 3/1996 | Hunt et al. |
| 5,513,272 A | 4/1996 | Bogosian, Jr. |
| 5,517,558 A | 5/1996 | Schalk |
| 5,533,123 A | 7/1996 | Force et al. |
| 5,534,855 A | 7/1996 | Shockley et al. |
| 5,546,471 A | 8/1996 | Merjanian |
| 5,546,523 A * | 8/1996 | Gatto ..................... 715/811 |
| 5,561,718 A | 10/1996 | Trew et al. |
| 5,572,597 A | 11/1996 | Chang et al. |
| 5,577,120 A | 11/1996 | Penzias |
| 5,578,808 A | 11/1996 | Taylor |
| 5,594,806 A | 1/1997 | Colbert |
| 5,598,474 A * | 1/1997 | Johnson .................. 713/186 |
| 5,602,933 A | 2/1997 | Blackwell et al. |
| 5,604,802 A | 2/1997 | Holloway |
| 5,613,012 A | 3/1997 | Hoffman et al. |
| 5,615,277 A * | 3/1997 | Hoffman .................. 382/115 |
| 5,621,812 A | 4/1997 | Deaton et al. |
| 5,635,723 A | 6/1997 | Fujieda et al. |
| 5,636,038 A | 6/1997 | Lynt et al. |
| 5,636,282 A | 6/1997 | Holmquist et al. |
| 5,647,364 A | 7/1997 | Schneider et al. |
| 5,650,217 A | 7/1997 | Skrivanek et al. |
| 5,655,116 A | 8/1997 | Kirk et al. |
| 5,677,989 A | 10/1997 | Rabin et al. |
| 5,719,950 A * | 2/1998 | Osten et al. .............. 382/115 |
| 5,745,555 A | 4/1998 | Mark |
| 5,748,780 A | 5/1998 | Stolfo |
| 5,757,917 A | 5/1998 | Rose et al. |
| 5,764,789 A | 6/1998 | Pare, Jr. et al. |
| 5,768,134 A | 6/1998 | Swaelens et al. |
| 5,770,849 A * | 6/1998 | Novis et al. .............. 235/492 |
| 5,787,187 A | 7/1998 | Bouchard et al. |
| 5,790,668 A | 8/1998 | Tomko |
| 5,794,207 A | 8/1998 | Walker et al. |
| 5,796,857 A | 8/1998 | Hara |
| 5,799,156 A | 8/1998 | Hogan et al. |
| D397,682 S | 9/1998 | Yotukura |
| 5,802,199 A | 9/1998 | Pare, Jr. et al. |
| 5,805,719 A | 9/1998 | Pare, Jr. et al. |
| D400,191 S | 10/1998 | Butts et al. |
| 5,822,737 A | 10/1998 | Ogram |
| 5,825,907 A | 10/1998 | Russo |
| 5,825,924 A | 10/1998 | Kobayashi |
| 5,826,241 A | 10/1998 | Stein et al. |
| 5,826,245 A | 10/1998 | Sandberg-Diment |
| 5,832,464 A | 11/1998 | Houvener et al. |

(56) References Cited

U.S. PATENT DOCUMENTS

| | | | |
|---|---|---|---|
| 5,838,812 A | 11/1998 | Pare, Jr. et al. | |
| 5,844,287 A | 12/1998 | Hassan et al. | |
| 5,845,005 A | 12/1998 | Setlak et al. | |
| 5,848,400 A | 12/1998 | Chang | |
| 5,850,442 A | 12/1998 | Muftic | |
| 5,870,723 A | 2/1999 | Pare, Jr. et al. | |
| 5,876,926 A * | 3/1999 | Beecham | 435/5 |
| 5,892,824 A | 4/1999 | Beatson et al. | |
| 5,892,838 A | 4/1999 | Brady | |
| 5,910,988 A * | 6/1999 | Ballard | 705/75 |
| 5,926,555 A | 7/1999 | Ort et al. | |
| 5,930,804 A | 7/1999 | Yu et al. | |
| 5,933,515 A | 8/1999 | Pu | |
| 5,935,071 A | 8/1999 | Schneider et al. | |
| 5,943,235 A | 8/1999 | Earl et al. | |
| 5,943,423 A * | 8/1999 | Muftic | 705/67 |
| 5,956,700 A | 9/1999 | Landry | |
| 5,982,914 A | 11/1999 | Lee et al. | |
| 5,986,746 A | 11/1999 | Metz et al. | |
| 5,991,372 A | 11/1999 | D'Ingianni et al. | |
| 6,011,858 A | 1/2000 | Stock et al. | |
| 6,012,039 A | 1/2000 | Hoffman et al. | |
| 6,016,476 A | 1/2000 | Maes et al. | |
| 6,023,688 A | 2/2000 | Ramachandran et al. | |
| 6,028,950 A * | 2/2000 | Merjanian | 382/126 |
| 6,029,195 A | 2/2000 | Herz | |
| 6,040,783 A | 3/2000 | Houvener et al. | |
| 6,041,309 A | 3/2000 | Laor | |
| 6,045,039 A | 4/2000 | Stinson et al. | |
| 6,052,675 A | 4/2000 | Checchio | |
| 6,064,751 A | 5/2000 | Smithies et al. | |
| 6,070,141 A * | 5/2000 | Houvener et al. | 705/76 |
| 6,072,894 A | 6/2000 | Payne | |
| 6,073,840 A | 6/2000 | Marion | |
| 6,084,967 A | 7/2000 | Kennedy et al. | |
| 6,105,010 A | 8/2000 | Musgrave | |
| 6,111,977 A | 8/2000 | Scott et al. | |
| 6,119,096 A | 9/2000 | Mann et al. | |
| 6,154,727 A * | 11/2000 | Karp et al. | 705/3 |
| 6,154,879 A | 11/2000 | Pare, Jr. et al. | |
| 6,182,076 B1 | 1/2001 | Yu et al. | |
| 6,192,142 B1 | 2/2001 | Pare, Jr. et al. | |
| 6,202,151 B1 | 3/2001 | Musgrave et al. | |
| 6,208,746 B1* | 3/2001 | Musgrave | 382/100 |
| 6,219,439 B1* | 4/2001 | Burger | 382/115 |
| 6,225,890 B1* | 5/2001 | Murphy | 340/426.19 |
| 6,230,148 B1 | 5/2001 | Pare, Jr. et al. | |
| 6,233,565 B1 | 5/2001 | Lewis et al. | |
| 6,233,618 B1 | 5/2001 | Shannon | |
| 6,256,737 B1 | 7/2001 | Bianco et al. | |
| 6,260,024 B1 | 7/2001 | Shkedy | |
| 6,268,788 B1 | 7/2001 | Gray | |
| 6,269,348 B1 | 7/2001 | Pare, Jr. et al. | |
| 6,275,944 B1 | 8/2001 | Kao et al. | |
| 6,310,966 B1 | 10/2001 | Dulude et al. | |
| 6,311,272 B1 | 10/2001 | Gressel | |
| 6,317,834 B1* | 11/2001 | Gennaro et al. | 713/186 |
| 6,327,578 B1 | 12/2001 | Linehan | |
| 6,366,682 B1 | 4/2002 | Hoffman et al. | |
| 6,377,228 B1 | 4/2002 | Jenkin et al. | |
| 6,397,198 B1 | 5/2002 | Hoffman et al. | |
| 6,411,728 B1 | 6/2002 | Lee et al. | |
| 6,496,107 B1 | 12/2002 | Himmelstein | |
| 6,522,772 B1 | 2/2003 | Morrison et al. | |
| 6,928,546 B1* | 8/2005 | Nanavati et al. | 713/186 |
| 7,133,792 B2* | 11/2006 | Murakami et al. | 702/104 |
| 7,152,787 B2 | 12/2006 | Cheng | |
| 2001/0000045 A1 | 3/2001 | Yu et al. | |
| 2001/0000535 A1 | 4/2001 | Lapsley et al. | |
| 2001/0011247 A1 | 8/2001 | O'Flaherty et al. | |
| 2001/0033661 A1* | 10/2001 | Prokoski | 380/258 |
| 2001/0034837 A1 | 10/2001 | Kausik et al. | |
| 2001/0044775 A1 | 11/2001 | Saito et al. | |
| 2001/0051924 A1* | 12/2001 | Uberti | 705/44 |
| 2003/0061172 A1 | 3/2003 | Robinson | |

FOREIGN PATENT DOCUMENTS

| | | |
|---|---|---|
| EP | 0651357 A1 | 5/1995 |
| EP | 0823701 A2 | 2/1998 |
| EP | 0652540 B1 | 9/2000 |
| JP | 57-212851 | 12/1982 |
| JP | 59-368860 | 2/1984 |
| JP | 61-187838 | 8/1986 |
| JP | 63-003369 | 1/1988 |
| JP | 63-120385 | 5/1988 |
| JP | 63-261492 | 10/1988 |
| JP | 03-189756 | 8/1991 |
| JP | 03-288954 | 12/1991 |
| JP | 04-322382 | 11/1992 |
| JP | 04-324583 | 11/1992 |
| JP | 05-062057 | 3/1993 |
| JP | 05-250524 | 9/1993 |
| JP | 06-149980 | 5/1994 |
| JP | 06-176135 | 6/1994 |
| JP | 11-003382 | 1/1999 |
| JP | 11-039540 | 2/1999 |
| JP | 11-154260 | 6/1999 |
| WO | WO 94/10659 A1 | 5/1994 |
| WO | WO 95/13591 A1 | 5/1995 |
| WO | WO 98/09227 A1 | 3/1998 |
| WO | WO 98/23062 A1 | 5/1998 |
| WO | WO 98/25227 A1 | 6/1998 |
| WO | WO 98/50875 A2 | 11/1998 |
| WO | WO 99/28847 A1 | 6/1999 |

OTHER PUBLICATIONS

Anonymous, "A Credit Union Points a Finger at Biometrics," Bank Network News, vol. 15, No. 16, Jan. 13, 1997, p. 2.

Anonymous, "Is it Time for Biometrics?", Banking Automation Bulletin for Europe, London, Sep. 1992, Issue 115, (ProQuest document ID 7415352), 1 page.

"Biometric ID Cards," store from Totse.com, Feb. 1996, 10 pages.

"Biometric Payment Firm Pay by Touch Secures $10 Million Funding," Finextra.com, Oct. 2003, 3 pages.

"Biometrics Comparison Chart," ncsc.dni.us, 2002, 2 pages.

Cavoukian, Ann, "Consumer Biometric Applications: A Discussion Paper," Information and Privacy Commissioner, Ontario, Canada, Sep. 1999, 65 pages.

Cavoukian, Ann, "Go Beyond Security—Build in Privacy: One Does Not Equal the Other," CardTec/SecurTech 96 Conference, Atlanta, GA, May 14-16, 1996, 7 pages.

Hall, Joseph, "Scanning Lets Fingerprints do Talking Scrambled Image Ensures Privacy Developer Says," Toronto Star, May 15, 1997, p. A6.

Holmes, James P., et al., "A Performance Evaluation of Biometric Identification Devices," Sandia National Laboratories, Jun. 1991, 27 pages.

Kolor, Joanna, "Biometric Technology Goes Live," Bank Network News, May 1, 1996, 7 pages.

Lange, et al., "Digital Identification: It's Now at our Fingertips," Electronic Engineering Times, No. 946, Mar. 24, 1997, p. 142.

"Pay by Touch Announces First UK Customer," Pay by Touch Press Release, May 11, 2004, 2 pages.

Radcliff, Deborah, "When Data Warehouse Become Open Houses," Software Magazine, vol. 16, No. 11, Nov. 26, 1996, 2pages.

"Recently Granted Patents in the USA," Transponder News, Sep. 1998, 5 pages.

Rechtin, Mark, "Fingerprint Technology Makes for Best ID System," Orange County Business Journal, vol. 22, Issue 51, Section 1, May 14, 1990, 3 pages (ProQuest Document ID 6020297).

Scally, Robert, "CompUSA Tests Fingerprinting to Help Secure Transactions," Discount Store News, vol. 36, No. 10, May 19, 1997, 2 pages.

Stosz, Jonathan D., et al., "Automated System for Fingerprint Authentication Using Pores and Ridge Structure," Proceedings of the International Society for Optical Engineering, vol. 2277, Jul. 28-29, 1994, pp. 210-223.

"Supermarkets and Shopper Registration Guide," Nocards.org, printed on Dec. 26, 2007, 19 pages.

(56) References Cited

OTHER PUBLICATIONS

"TCP Protocol Overview," printed on Dec. 26, 2007, 3 pages.
"Veridicom Showcases New Customers and Applications at COMDEX," Veridicom Press Release, Nov. 16, 1998, 3 pages.
"What Are Food Stamps?", Virginia Department of Social Services, Nov. 10, 2005, 1 page.
"Why do you call them "registration and monitoring" programs?", Frequently Asked Questions, Nocards.org, printed on Feb. 26, 2007, 1 page.

* cited by examiner

BIOMETRIC FINANCIAL TRANSACTION SYSTEM AND METHOD

CROSS-REFERENCE

This application is a continuation of U.S. application Ser. No. 13/284,219, filed Oct. 28, 2011, now issued U.S. Pat. No. 8,452,680, issued on May 8, 2013, which is a continuation of U.S. application Ser. No. 13/108,703, filed May 16, 2011, now issued U.S. Pat. No. 8,073,756, issued on Dec. 6, 2011, which is a continuation of U.S. application Ser. No. 12/423,628, filed Apr. 14, 2009, now issued U.S. Pat. No. 7,970,678, issued on Jun. 28, 2011, which is a division of U.S. application Ser. No. 09/871,241, filed May 30, 2001, now issued U.S. Pat. No. 7,565,329, issued on Jul. 21, 2009, which claims the benefit of U.S. provisional application Ser. No. 60/208,680, filed May 31, 2000, herein incorporated by reference.

FIELD OF THE INVENTION

This invention relates to the field of tokenless biometric financial transactions. Specifically, this invention is directed towards a system and method for processing tokenless financial transactions using a wired or wireless communication system such as a conventional telephone, a cellular telephone, or a wireless personal digital assistant (PDA) wherein a biometric, such as a finger image or voice print, is used to authorize the transaction.

BACKGROUND OF THE INVENTION

There is an increasing need for consumers to be able to conveniently and securely purchase goods and services over the telephone (be it wired or wireless) or via a wireless PDA such as a Palm Pilot.

Conventionally, purchases made over the telephone are accomplished via the use of a credit card. The consumer calls the merchant, places an order for the appropriate goods and services, and then chooses a credit card with which to pay for the transaction. The consumer then reads the account number and expiration date off the credit card to the customer service representative at the merchant, who copies this information down and uses it to charge the account.

Purchases made using a wireless PDA or other device for accessing the Internet follow a similar pattern: the consumer connects to the merchant's web site, places an order, and then fills in a "form" with credit card account number and expiration information. The merchant's computer system uses this information to charge the credit card account.

There are numerous problems with this conventional approach. First, the system is inconvenient for the consumer, in that the consumer must recite or enter a significant amount of information. Second, the system is insecure, in that the credit card account information is generally transmitted "in the clear," making it subject to loss or compromise via interception. Third, the system is inflexible, in that the only payment mechanism that lends itself to use is the credit card; it is difficult, for example, to use one's checking account to pay via telephone.

A fourth problem is that transactions made without the card being physically present (as in the case of a telephone or Internet order) are charged a higher "discount rate" than transactions where the card is present. The discount rate is the amount that the credit card associations, issuing banks, acquiring banks, and third-party transaction processors collectively charge the merchant on each transaction, generally expressed as a percentage of the gross transaction amount. Discount rates of 3%-5% for card-not-present transactions are common.

The fifth, and perhaps largest, problem is that the consumer can repudiate the transaction at a later date, leaving the merchant liable for the amount of the transaction. That is, a consumer can order goods or services via telephone or the Internet, pay using his or her credit card, and then later dispute the transaction. In the event of a dispute, credit card association rules place the burden on the merchant to produce a signed receipt showing that the customer authorized the transaction. Of course, in the case where the order took place over the telephone or the Internet, no such signed receipt exists. As a result, the consumer can always claim that they didn't authorize the transaction. Such a claim is called a "chargeback." In the event of a chargeback, the merchant not only ends up losing the transaction amount, but generally also must pay a chargeback fee of $10-$25.

A sixth problem is that many previously proposed solutions to the problems cited require the consumer to physically possess a personalized, portable, man-made memory device—referred to in this specification as a "token"—to carry out a transaction. "Personalized" means that a token that contains in memory information that is in some way unique to the consumer. An example of personalized data include a credit card number, a checking account number, or any other unique account number. Example tokens include credit cards, debit cards, paper checks, and smart cards. A token can also be a PDA or wireless telephone that has programmed with information personalized to the consumer that is used to complete a financial transaction. The problems with requiring the use of a token to complete a financial transaction are numerous: the consumer must carry the token, which may be cumbersome; the loss or theft of a consumer's token financially incapacitates the consumer; and stealing a consumer's token may allow a thief to make fraudulent charges using the token. Tokenless transaction systems are known in the art; examples include U.S. Pat. No. 5,613,012 to Hoffman et al., U.S. Pat. No. 5,838,812 to Pare, Jr. et al., U.S. Pat. No. 5,870,723 to Pare, Jr. et al., U.S. Pat. No. 6,230,148 to Pare, Jr. et al., and U.S. Pat. No. 6,154,879 to Pare, Jr. et al., all of which are assigned to VeriStar Corporation, the assignee of the instant invention, and all of which are incorporated by reference.

As a result, there is a need for a new electronic financial transaction system that solves these problems for telephone and wireless PDA-style transactions. Accordingly, it is an object of this invention to provide a new system and method for biometric financial transactions.

In particular, it is an object of the invention that each transaction authorized using the invention cannot be repudiated by the consumer, thus eliminating chargebacks.

It is another object of the invention that the system and method be convenient for the consumer, eliminating the need to recite or otherwise enter credit card or other account numbers into a telephone or PDA.

It is another object of the invention that the system and method be secure, eliminating the possibility of fraud via intercepting transmissions from the telephone or PDA.

It is still another object of the invention that the system and method provide the flexibility of supporting multiple types of financial accounts, e.g., credit cards, debit cards, and checking (ACH) accounts.

It is another object of this invention that the consumer be able to complete a transaction on a tokenless basis. As such, this tokenless transaction occurs without the consumer being required to possess or present any man-made, portable devices which contain in memory data that is personalized to the consumer, i.e., tokens. Although the consumer may optionally possess such tokens, the invention is expressly designed to function without requiring their use and as such, the invention is designed to be tokenless.

It is yet another object of the invention that the system and method, through its superior security and non-repudiation capabilities, justify a reduced discount rate for the merchant.

It is still another object of the invention that it be easy to integrate with existing merchant computer, information, and payment systems.

SUMMARY OF THE INVENTION

This invention provides a method for tokenless biometric authorization of an electronic transaction between a consumer and a merchant using an electronic identicator and an access device. The method comprises the following steps: In a consumer registration step, a consumer registers with the electronic identicator at least one registration biometric sample taken directly from the consumer's person. In a first communications establishment step, the consumer and merchant establish communications with each other via an access device capable of biometric input, and wherein the access device is not required to contain in memory any data that is personalized to the consumer. In a proposal step, the merchant proposes a commercial transaction to the consumer via the access device. In a first access device identification step, the access device communicates to the merchant an identification code associated with the access device. In a second communications establishment step, after the consumer and merchant have agreed on the proposed commercial transaction, the consumer and the electronic identicator use the access device to establish communications with each other. In a second access device identification step, the access device communicates to the electronic identicator the identification code associated with the access device. In a consumer identification step, the electronic identicator compares a bid biometric sample taken directly from the consumer's person with at least one previously registered biometric sample to produce a successful or failed identification of the consumer. In an information forwarding step, upon successful identification of the consumer, the electronic identicator electronically forwards information regarding the consumer to the merchant. Upon successful identification of the consumer, these steps enable a biometrically authorized electronic financial transaction without the consumer being required to present any personalized man-made memory tokens.

Optionally, the electronic identicator may perform an electronic financial transaction authorization. In this embodiment, there is a transaction forwarding step, the merchant forwards information regarding the commercial transaction to the electronic identicator. In an identification code forwarding step, the merchant communicates to the electronic identicator the identification code associated with the access device that was previously communicated to the merchant. In an association step, the identification code associated with the access device is used to associate the biometric identification accomplished in the consumer identification step with the information regarding the commercial transaction. Finally, there is a financial transaction authorization step: the electronic identicator executes a financial transaction on behalf of the merchant.

Alternatively, the merchant may optionally perform an electronic financial transaction authorization. In this embodiment, there is an identification code forwarding step, wherein the electronic identicator forwards to the merchant the identification code associated with the access device that was previously communicated to the electronic identicator. In an association step, the identification codes associated with the access device are used to associate the information regarding the consumer with the commercial transaction. In a financial transaction authorization step, the merchant executes a financial transaction.

The invention also includes a system for tokenless biometric authorization of an electronic transaction between a consumer and a merchant. The system includes an electronic identicator, comprising at least one computer further comprising at least one database wherein the consumer registers at least one registration biometric sample taken directly from the consumer's person. It also includes an access device capable of establishing communications between the consumer and the merchant, and between the consumer and the electronic identicator, and further comprising biometric input means, said access device not being required to contain in memory any data that is personalized to the consumer. There is a communication means for enabling communications between the consumer and the merchant, and between the consumer and the electronic identicator, and capable of transmission of a bid biometric sample obtained by the access device from the person of the consumer to the electronic identicator. A comparator engine is used to compare a bid biometric sample to at least one registration biometric sample. An execution module is used for authorizing a transfer of a transaction amount from a financial account of the consumer to a financial account of the payor. The system enables a financial transaction to be conducted without the consumer being required to possess any man-made tokens containing information in memory that is personalized to the consumer.

The electronic identicator can include means responsive to a comparison matching the bid biometric sample to the registration biometric sample to forward information to the merchant regarding the consumer.

Information forwarded regarding the consumer may comprise a previously registered financial account identifier belonging to the consumer, or the consumer's age, or name, or address. It may also indicate the success or failure of a financial transaction. Financial account identifiers may comprise a credit card number, a debit card number, or a bank account number.

The access device may be a wireline telephone, a wireless telephone, a two-way pager, a personal digital assistant, or a personal computer. Identification codes associated with an access may include telephone numbers, electronic serial numbers (ESN), a hardware identification code, or encryption of a challenge message using a private key.

Communication of the identification code may be accomplished via caller ID, and the first and second communication establishment steps may be implemented using a telephone call, three-way calling, induced three-way calling, or packet switching.

Biometrics used in the invention may include finger images, facial images, retinal images, iris images, or voiceprints.

The execution module may optionally be located or operated by the merchant, or by the electronic identicator, or by a third party.

The foregoing and other objects, features and advantages of the invention will become more readily apparent from the following detailed description of a preferred embodiment of the invention which proceeds with reference to the accompanying drawings.

DETAILED DESCRIPTION

Overall Architecture

Figure 1:
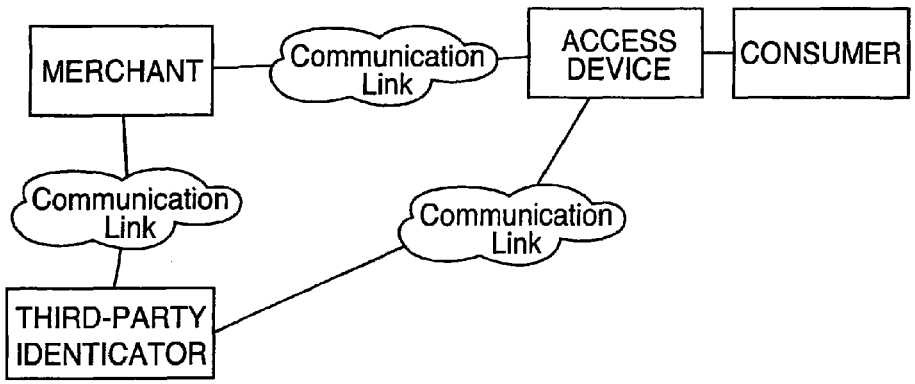
FIG. 1 shows the overall collection of elements comprising the system.
Figure 2:
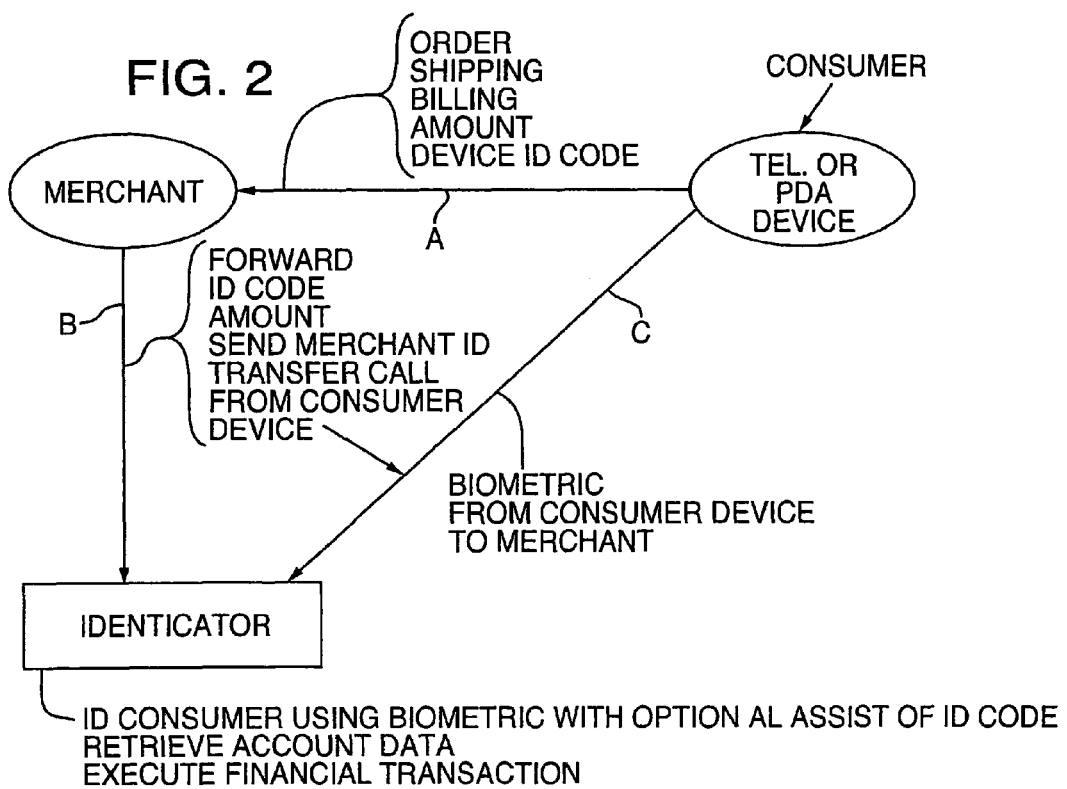
FIGS. 2, 3, and 4 illustrate examples of operation of the system of FIG. 1 according to the invention.
Figure 3:
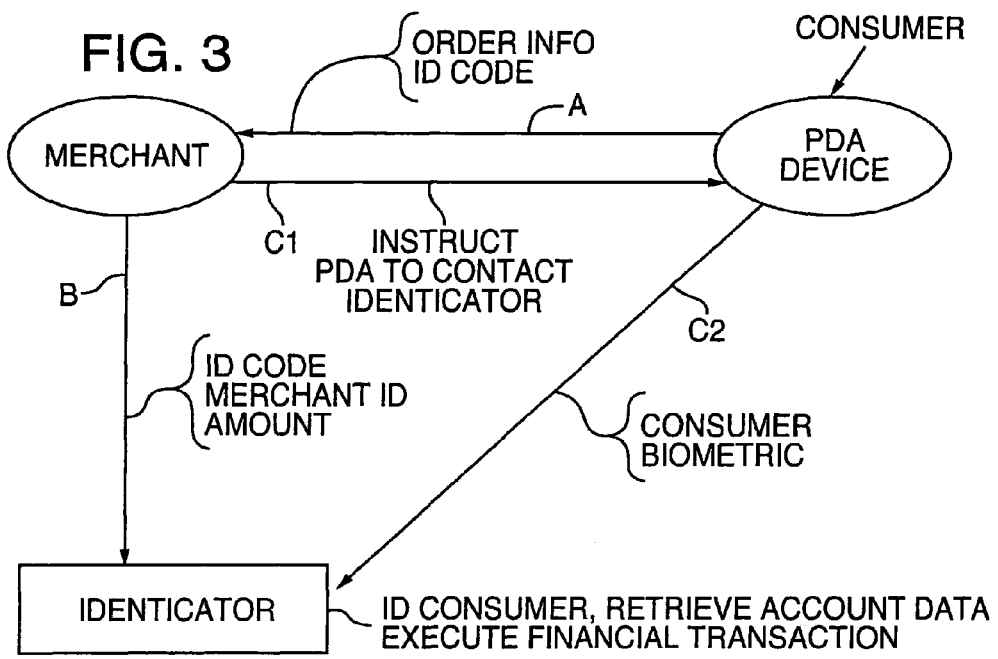
Figure 4:
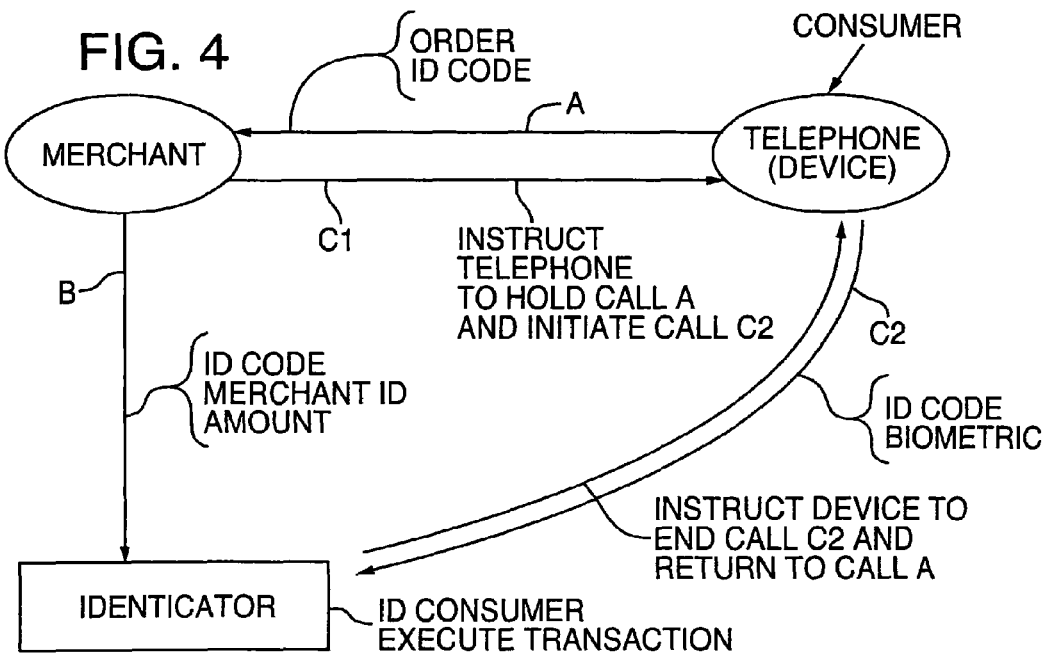

As shown in FIG. 1, the invention comprises the following components. There is at least one consumer who is able to use the invention for purchasing goods or services. Similarly, there is at least one merchant who is able to fulfill orders from the consumer. The consumer has access to an access device. As described in greater detail below, an access device is simply a device that is capable of both communicating an order to a merchant and also accepting a biometric from the consumer. A biometric or a biometric sample is any unique human characteristic of which a scan or image is taken directly from the person. The biometric or biometric sample may be, but is not limited to, any of the following: a voice print, a fingerprint, a retinal image, an iris image, a facial image.

A third-party identicator provides the ability to accept biometric and other data as input, to identify the consumer from this data, and to either complete a financial transaction on behalf of the merchant or to provide information to the merchant to enable the merchant to complete a financial transaction. Throughout this specification the terms "third-party identicator" and "electronic identicator" are used interchangeably; it is understood that the electronic identicator may be owned and/or operated by the merchant, the consumer, or a third party, without loss of generality.

Communication Links

Communication links exist or can be established between the access device and the merchant, the access device and the third-party identicator, and the merchant and the third-party identicator. A communication link can be a permanent connection (e.g., a leased line), a temporary switched-circuit connection (e.g., a dialup telephone call), or a virtual connection (e.g., via packet switching). Encryption can be employed on all communication links to protect sensitive data, as is standard in the industry.

Access Device

An access device is any device that is capable of communicating an order to a merchant and also accepting a biometric sample from the consumer. Different access devices are preferable in different situations. The access device is not required to contain in memory any data which is personalized to or unique to the consumer in order for the consumer to complete a financial transaction. Example access devices include:

A standard wireline telephone. A consumer can use such a device to call a merchant and place an order, as is done today. Additionally, it can be used as a biometric input device using the consumer's voice as a biometric.

A wireless or cellular telephone. Just like a standard wireline telephone, a wireless telephone can also be used as an access device using voice biometrics.

A wireless or cellular telephone with a built-in finger image scanner or other biometric sensor. This is like the example above, but uses a biometric other than voice, e.g., a finger image.

A wireless personal digital assistant (PDA) with a microphone or other biometric sensor. The wireless PDA can be used to enter and communicate an order to a merchant, and a microphone or other biometric sensor can be used to input a biometric. Other access devices will be apparent to those of ordinary skill in the art.

Every access device possesses an identification (ID) code. This ID code is preferably unique to the device, but is not required to be. Examples of ID codes include a digital certificate stored in a PDA or wireless telephone, a telephone or ESN number stored in a wireless telephone, or a telephone number in the case of a wire-line phone. Note that in this last example the ID code (the telephone number) is not unique to the device (the telephone) but is rather unique to the telephone line.

Third-Party Identicator

The third-party identicator is a data and call-processing center comprising a database of biometric and financial account information for at least one, and ordinarily for many consumers.

An identicator can be a single computer that serves a particular merchant or a large collection of computers that serve a number of different merchants. The third-party identicator accepts queries of biometric data and identifies consumers from this data. Once identified, the third-party identicator retrieves financial account data associated with that consumer. This financial account information either is then used to directly charge the financial account, or is provided to the merchant to charge the account.

Third-party identicators are known in the art; an example third-party identicator is given in section 1.5 "System Description: Data Processing Center" in U.S. Pat. No. 5,613,012 to Hoffman, et al., which is assigned to the same entity that this invention is assigned to, and which is hereby incorporated by reference.

Use of the System Via Telephone Access Device

In one embodiment a telephone is the access device used. Use of the system in this embodiment proceeds as follows.

1. The consumer uses the access device (telephone) to contact the merchant.

2. The consumer and the merchant work out and agree upon the details of the transaction, including the goods or services to be ordered, the ship to and bill to addresses, and the transaction amount.

3. The merchant receives the ID code from the access device. In one embodiment, this is via caller ID.

4. The merchant sends the ID code, the merchant identifying information, and the transaction amount to the third-party identicator. This information may be sent via an out-of-band channel (e.g., a separate network connection or via a virtual private network) or it may be passed in-band at the start of step 5, below.

5. The merchant transfers the telephone call to the third-party identicator.

6. The third-party identicator prompts the consumer to enter their biometric. In one embodiment this biometric is a finger image. In another embodiment it is a voiceprint. Other biometrics are known. This biometric information is sent to the third-party identicator.

7. The third-party identicator uses the biometric information to identify the consumer. In the event that the consumer cannot be identified from the supplied biometric, the third-party identicator prompts the consumer to try again. If the consumer cannot be identified after repeated tries, the third-party identicator transfers the call to a human customer service assistant, who can use other means to identify the consumer.

8. In the event of a successful identification the third-party identicator retrieves account information for the consumer.

Account information consists of credit card or other financial account data sufficient to complete a financial transaction.

9. If necessary, the third-party identicator uses the ID to assist in matching up the transaction information (merchant identification information and amount) with the individual.

10. In one embodiment, the third-party identicator performs a financial transaction using the retrieved financial account information. In another embodiment, the third-party identicator returns this financial account information to the merchant so that the merchant can complete a financial transaction.

Use of System via Personal Digital Assistant

In another embodiment, a wireless PDA is the access device used. As discussed above, different biometrics are possible. For illustrative purposes, a voice biometric is used in this embodiment. Use of the system in this embodiment proceeds as follows:

1. The consumer uses the access device (wireless PDA) to contact the merchant's web site or its equivalent.

2. The consumer and the merchant work out and agree upon the details of the transaction, including the goods or services to be ordered, the ship to and bill to addresses, and the transaction amount.

3. The merchant receives the ID code from the access device. In this embodiment, this is either a digital certificate identification or a number stored in the device.

4. The merchant sends the ID code, the merchant identifying information, and the transaction amount to the third-party identicator.

5. The merchant sends a message to the device indicating that the device should contact the third-party identicator.

6. The third-party identicator sends a message to the device instructing it to prompt the consumer to enter his or her biometric. As described above, a voice biometric is used for illustrative purposes in this embodiment, but other biometrics are possible. This biometric information is sent to the third-party identicator.

7. The third-party identicator uses the biometric information to identify the consumer. In the event that the consumer cannot be identified from the supplied biometric, the third-party identicator prompts the consumer to try again. If the consumer cannot be identified after repeated tries, the third-party identicator alerts a human customer service assistant, who can use other means to identify the consumer.

8. In the event of a successful identification, the third-party identicator retrieves account information for the consumer. Account information may consist of credit card account number or other financial account data sufficient to complete a financial transaction.

9. If necessary, the third-party identicator uses the ID to assist in matching up the transaction information (merchant identification information and amount) with the individual.

10. In one embodiment, the third-party identicator performs a financial transaction using the retrieved financial account information. In another embodiment, the third-party identicator returns this financial account information to the merchant so that the merchant can complete a financial transaction.

Use of System Via Telephone with Induced Three-Way Calling

In another embodiment, a telephone having a feature known as "induced three-way calling is the access device used. In this embodiment, an external entity (e.g., the merchant) can request that the telephone put the current connection on hold and then dial out and establish another connection. While this feature does not exist in current generation telephones, implementation of such a feature would be straightforward for one of ordinary skill in the art. For illustrative purposes, a voice biometric is used in this embodiment. Use of the system in this embodiment proceeds as follows:

1. The consumer uses the access device (telephone) to contact the merchant.

2. The consumer and the merchant work out the details of the transaction, including the goods or services to be ordered, the ship to and bill to addresses, and the transaction amount.

3. The merchant receives the ID code from the access device. In one embodiment, this is via caller ID.

4. The merchant sends the ID code, the merchant identifying information, and the transaction amount to the third-party identicator. This information may be sent via an out-of-band channel (e.g., a separate network connection or via a virtual private network) or it may be passed in-band at the start of step 5, below.

5. The merchant sends a message to the access device (telephone) instructing it to put the current call to the merchant on hold and to call the third-party identicator.

6. The third-party identicator obtains the access device ID from the access device. In one embodiment, this is via caller ID.

7. The third-party identicator prompts the consumer to enter their biometric. In one embodiment this biometric is a finger image. In another embodiment it is a voiceprint. Other biometrics are known. This biometric information is sent to the third-party identicator.

8. The third-party identicator uses the biometric information to identify the consumer. In the event that the consumer cannot be identified from the supplied biometric, the third-party identicator prompts the consumer to try again. If the consumer cannot be identified after repeated tries, the third-party identicator transfers the call to a human customer service assistant, who can use other means to identify the consumer.

9. In the event of a successful identification the third-party identicator retrieves account information for the consumer. Account information consists of credit card or other financial account data sufficient to complete a financial transaction.

10. If necessary, the third-party identicator uses the ID to assist in matching up the transaction information (merchant identification information and amount) with the individual.

11. In one embodiment, the third-party identicator performs a financial transaction using the retrieved financial account information. In another embodiment, the third-party identicator returns this financial account information to the merchant so that the merchant can complete a financial transaction.

12. The third-party identicator sends a message to the access device instructing it to terminate the call and resume the call with the merchant.

13. The merchant now verifies that the transaction completed successfully.

From the foregoing it will be appreciated how the objects of the invention are met. As can be seen from the above, the invention is marked advantageous over existing systems in numerous ways:

First, because each transaction is authorized using a biometric received from the consumer's person, the transaction cannot be repudiated, eliminating chargebacks.

Second, the invention is convenient for the consumer, in that the third-party identicator handles all financial account information, eliminating the need to recite or otherwise enter credit card or other account numbers into a telephone or PDA.

Third, the use of biometrics and encryption provides security, eliminating the possibility of fraud via intercepting transmissions from the telephone or PDA.

Fourth, the system supports the use of multiple types of financial accounts, providing flexibility for the consumer.

Fifth, through its superior security and non-repudiation capabilities, the invention justifies a reduced discount rate for the merchant.

Sixth, by using ordinary telephone connections or existing wireless connections, the invention is easy to integrate with existing merchant computer, information, and payment systems.

Seventh, the invention does not require the consumer to use or possess any portable, man-made tokens containing data personalized to the user in order to complete a financial transaction.

Although the invention has been described with respect to a particular biometric electronic transaction system and method for its use, it will be appreciated that various modifications of the system and method are possible without departing from the invention.

What is claimed is:

1. A method, comprising:
   receiving, at a data processing center via a first device, a first request to enable a transaction, wherein the first request includes data pertaining to a transaction between an entity and an individual who has registered with the data processing center at least a registered biometric sample, wherein the first device is operated by the entity;
   receiving, at the data processing center, a second request to enable the transaction, wherein the second request is received via a second device in short-range communication with a third device, wherein the second device enables a communication link between the third device and the data processing center and the third device is a wireless device operated by the individual;
   receiving, at the data processing center from the second device, a biometric sample, wherein the biometric sample is transmitted from the third device to the second device via short-range communication;
   comparing, at the data processing center, the biometric sample with one or more registered biometric samples to produce a successful or failed identification of the individual;
   enabling the transaction at the data processing center, based upon a successful identification of the individual and according to the data pertaining to the transaction; and wherein upon the successful identification of the individual, the enabling comprises at least one of:
      retrieving, at the data processing center, financial account data that the individual has registered with the data processing center and that is associated with the registered biometric sample; and
      forwarding, to the first device, the retrieved financial account data.

2. The method of claim 1, wherein upon the successful identification of the individual, the enabling comprises utilizing the received transaction data and consumer financial account data that the individual has registered with the data processing center and that is associated with the registered biometric sample to perform the transaction.

3. The method of claim 1, comprising indicating that the individual authorizes the transaction with the received biometric sample.

4. The method of claim 1, wherein the enabling comprises at least one of:
   confirming that the individual has authorized the transaction via provision of the biometric sample and
   denying the individual an ability to repudiate the transaction.

5. The method of claim 1, wherein the second device is operated by the entity.

6. The method of claim 1, wherein the second device is operated by a third party.

7. The method of claim 1, wherein upon the successful identification of the individual, the enabling comprises at least one of:
   retrieving, at the data processing center, age data that the individual has registered with the data processing center and that is associated with the registered biometric sample; and
   forwarding, to the first device, the retrieved age data.

8. The method of claim 1, wherein the data pertaining to the transaction includes at least one of: individual device identifying data, wherein the individual device identifying data is used to match the first request and second request; goods or services to be purchased; a shipping address; a billing address; the transaction amount; and first device identifying data.

9. A method, comprising:
   receiving, at a data processing center via an entity device, a request to enable a transaction, wherein the request includes data pertaining to a transaction between an entity and an individual, the individual having registered with the data processing center a first biometric sample;
   prompting, at an individual device, the individual to present a second biometric sample, wherein the prompt is communicated via a system device in short-range communication with the individual device, wherein the system device enables a communication link between the individual device and the data processing center;
   receiving, at the data processing center from the system device, the second biometric sample, wherein the second biometric sample is transmitted from the individual device to the system device via short-range communication;
   comparing, at the data processing center, the second biometric sample with the first biometric sample to produce a successful or failed identification of the individual;
   enabling, at the data processing center based upon a successful identification of the individual and according to the data pertaining to the transaction, the transaction;
   and wherein the enabling comprising at least one of:
      retrieving, at the data processing center, financial account data that the individual has registered with the data processing center and that is associated with the first biometric sample; and
      forwarding, to the entity device, the retrieved financial account data.

10. The method of claim 9, comprising the data processing center initiating the prompting.

11. The method of claim 9, comprising at least one of:
   the data pertaining to the transaction including individual device identifying data; and
   the data processing center using the individual device identifying data to identify the individual device to prompt.

12. The method of claim 9, wherein the enabling comprises utilizing the received transaction data and consumer financial account data that the individual has registered with the data processing center and that is associated with the first biometric data to perform the transaction.

13. A method, comprising:
- receiving, at a data processing center via an entity device, a first request to enable a transaction, including data pertaining to the transaction between an entity and an individual;
- receiving, at the data processing center, a second request to enable the transaction, wherein the second request is received via an individual device in short-range communication with a virtual connection device that enables a communication link between the individual device and the data processing center;
- receiving, at the data processing center via the virtual connection device, a biometric sample wherein the biometric sample is transmitted from the individual device to the virtual connection device via short-range communication;
- comparing, at the data processing center, the biometric sample with one or more registered biometric samples to produce a successful or failed identification of the individual; and
- enabling, at the data processing center based upon a successful identification of the individual and according to the data pertaining to the transaction, the transaction; and
- wherein the virtual connection device that enables the communication link between the individual device and the data processing center is operated by one or more of the data processing center and a third party.

14. The method of claim 13, wherein the individual device is a wireless device operated by the individual.

15. The method of claim 13, comprising the data processing center prompting the individual device via the virtual connection device to present the biometric sample.

16. The method of claim 13, comprising negotiating the transaction between the entity and the individual via the entity device and the individual device.

17. The method of claim 16, wherein the entity device and the individual device communicate via the virtual connection device.

* * * * *